United States Patent [19]

Theobald et al.

[11] Patent Number: 4,954,633
[45] Date of Patent: Sep. 4, 1990

[54] ISOXAZOLINES AS INTERMEDIATES TO FURANS

[75] Inventors: Hans Theobald, Limburgerhof; Rainer Becker, Bad Durkheim; Walter Himmele, Walldorf, all of Fed. Rep. of Germany

[73] Assignee: BASF Aktiengesellschaft, Fed. Rep. of Germany

[21] Appl. No.: 384,910

[22] Filed: Jul. 25, 1989

Related U.S. Application Data

[63] Continuation of Ser. No. 270,475, Nov. 4, 1988, abandoned, which is a continuation of Ser. No. 154,431, Feb. 8, 1988, abandoned, which is a continuation of Ser. No. 813,981, Dec. 27, 1985, abandoned.

[30] Foreign Application Priority Data

Dec. 29, 1984 [DE]  Fed. Rep. of Germany ....... 3447793
Apr. 20, 1985 [DE]  Fed. Rep. of Germany ....... 3514384

[51] Int. Cl.$^5$ ............................................. C07D 261/04
[52] U.S. Cl. ..................................... 548/240; 549/497
[58] Field of Search ............................................ 548/240

[56] References Cited

U.S. PATENT DOCUMENTS 3,415,821  12/1968  Davis et al. ........................ 548/309

FOREIGN PATENT DOCUMENTS 3447793  7/1986  Fed. Rep. of Germany .
3514384  10/1986  Fed. Rep. of Germany .
3546371  7/1987  Fed. Rep. of Germany .
1385507  2/1975  United Kingdom .

OTHER PUBLICATIONS

*Chemie der Pflanzenschutz-und Schadlings bekampfungsmittel* by R. Wegler, pp. 76, 77, 104, 154, (1981).

Chemical Abstract for JP 71-35872, (2/3/68).
Curran, *JACS*, 105, p. 5826, (1983).
Houk et al., *JACS*, 106, p. 3880, (1984).
Elliott et al., *J. Chem. Soc.*, p. 2551, (1971).
Curran et al., *Tet. Lett.*, 24, p. 2079, (1983).
Wolf et al., Chemical Abstracts, vol. 107, No. 154552w, (1987).
Theobald et al., Chemical Abstracts, vol. 105, No. 172440w, (1986).
Jäger et al., Chemical Abstracts, vol. 95, No. 96934t, (1981).
Jäger et al., *Angew. Chem. Int. Ed. Engl.*, 20, p. 601, (1981).

*Primary Examiner*—Mukund J. Shah
*Assistant Examiner*—E. Bernhardt
*Attorney, Agent, or Firm*—Keil & Weinkauf

[57] ABSTRACT

Isoxazolines of the general formula II

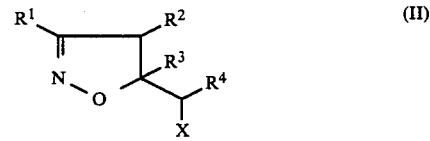

in which $R^1$, $R^2$, $R^3$ and $R^4$ are each unsubstituted or halogen-, haloalkyl-, alkoxy-, haloalkoxy-, nitro-, cyano-, dialkylphosphonyl- or alkoxycarbonyl-substituted alkyl, aryl, aralkyl, alkoxycarbonyl or dialkoxyphosphonyl, $R^2$ and $R^4$ are each also hydrogen and $R^3$ is also hydroxyalkyl which is unblocked or blocked by a detachable protective group or is haloalkyl, X is hydrogen or a detachable protective group, are used to prepare furans.

3 Claims, No Drawings

ISOXAZOLINES AS INTERMEDIATES TO FURANS

This application is a file wrapper continuation of application Ser. No. 270,475, filed Nov. 4, 1988, now abandoned, which is a file wrapper continuation of Ser. No. 154,431, filed Feb. 8, 1988, now abandoned, which is a file wrapper continuation of application Ser. No. 813,981, filed Dec. 27, 1985, now abandoned.

Furans with up to four substituents and the general formula (I)

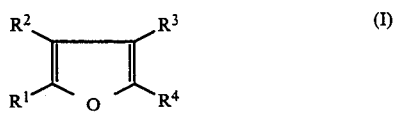

in which $R^1$ to $R^4$ are each hydrogen or unsubstituted or halogen-, haloalkyl-, alkoxy-, haloalkoxy-, nitro-, cyano-, dialkylphosphonyl- or alkoxycarbonyl-substituted alkyl, aryl, aralkyl, alkoxycarbonyl or dialkoxyphosphonyl, $R^3$ is also hydroxyalkyl which is unblocked or blocked by a detachable protective group, are needed as precursors, for example for preparing crop protection agents. It is known that furans can be prepared from 1,4-diketones by cyclization (Comprehensive Heterocyclic Chemistry 4 (1984) 657 et seq. In the synthesis of in particular asymmetrically substituted furans (for example 2,4-disubstitution), the preparation of the starting materials required is difficult. For that reason, various methods aree recommended for preparing for example 2-benzyl-4-hydroxymethylfuran, a desirable intermediate for insecticide syntheses (JCS (c) 1971, 2551; Wegler 7 (1981) 76; German Laid-Open Application DOS 2,122,823). However, all these methods have serious disadvantages (multistage syntheses with moderate overall yield; safety problems due to high temperatures; formation of isomers).

It is an object of the present invention to specify a process for preparing substituted furans which uses readily available starting materials and is easy to carry out.

We have found that this object is achieved by obtaining furans of the abovementioned kind advantageously by hydrrogenating a corresponding isoxazoline of the formula II

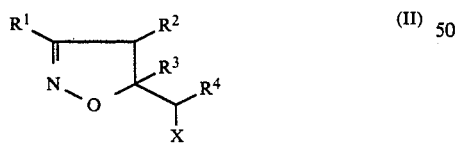

in which X is hydroxyl, halogen or hydroxyl which is blocked by a detachable protective group.

The hydrogenation of substituted isoxazolines is known in principle (J. Am. Chem. Soc. 104 (1982), 4024; Tetrahedron Lett. 23 (1982), 3123 and 24 (1983), 1337) and has also been used for the synthesis of heterocycles. For instance, suitably substituted isoxazolines can be made to undergo hydrogenating cleavage to give pyrones (U.S. Pat. No. 4,136,114), pyridines (J. Org. Chem. 36 (1971), 2784), pyrimidines and pyrimidones (J. Pharm. Soc. Jap. 83 (1963), 471 or Ann. Chim. 60 (1970), 393), pyrroles (Ann. Chim. 56 (1966), 858), pyrazoles (Chem. Ber. 106 (1973), 332 or Tetrahedron 29 (1973), 4291), imidazoles (Ann. Chim. 60 (1970), 343) or even furanones (Tetrahedron Lett. (1983) 2079 or (1966) 233 or (1967) 327 or Gazetta (1966) 1073).

The formation of the furans according to the invention is not observed in any of these hydrogenations, although suitably substituted starting materials (i.e. 5-hydroxymethyl-substituted isoxazolines—e.g. J. Am. Chem. Soc. 105 (1983), 5826–5833); compound 18a) have been used in this reaction. Only Acta Chem. Scand. B 36 (1982), 1–14 describes an acid-catalyzed rearrangement of isoxazolines under nonhydrogenating conditions where a specific substitution produced a furan derivative via a diketone intermediate. Slightly different substitution patterns produced not furan derivatives but furanones and cyclopentenones.

Isoxazolines of the general formula II, except those in which $R^1$ or $R^3$ is hydrogen, are novel substances. It will be readily understood that in those cases where $R^3$ is etherified or esterified hydroxymethyl and at the same time X is blocked hydroxyl an etherification or esterification may have taken place with a bifunctional reactant together with cyclization. Depending on the specific method, this result can be obtained directly or it is possible to isolate the hydroxyketone III

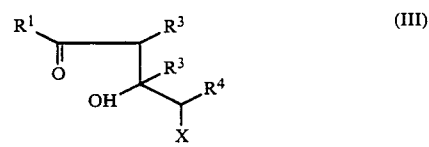

as an intermediate and to obtain the desired furan derivative in a subsequent step:

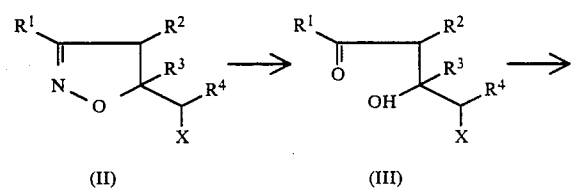

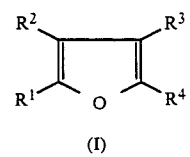

In the case of the abovementioned 2-benzyl-4-hydroxymethylfuran the reaction can be represented as follows:

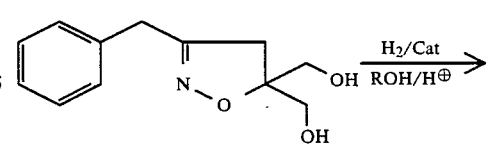

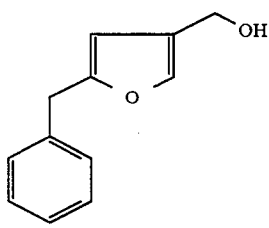

The smooth course of this reaction is, inter alia, also surprising because hitherto the hydrogenation of specifically substituted isoxazoles has merely been described as a method of synthesizing the hydrofuran-3-ones (Tetrahedron Lett. (1983) 2079; Tetrahedron Lett. (1966) 233; Tetrahedron Lett. (1967) 327; Gazetta (1966) 1073):

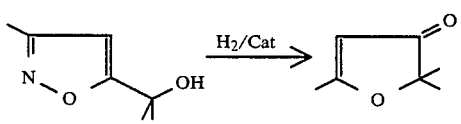

Furthermore, a specific isoxazoline substitution in the reduction with TiCl$_3$ produced 2,5-disubstituted furans (Acta Chem. Scand. B 36 (1982):

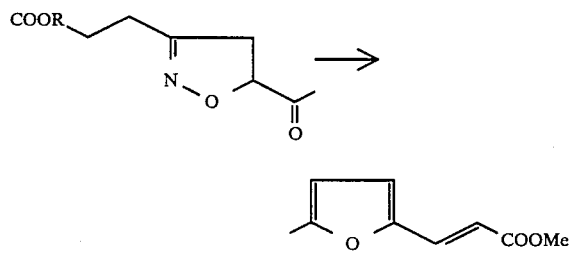

The novel precursors II are prepared in particular as follows:

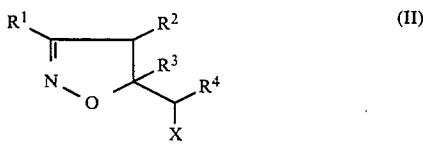

can be obtained for example by the method in Heterocycles 12 (1979), 1243 et seq. by reacting nitrile oxides with certain olefins as shown by

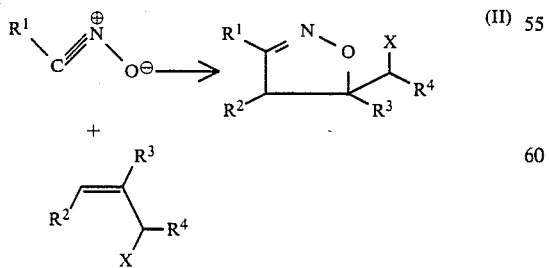

In the preceding reaction, X is hydroxyl which is unblocked or blocked by a detachable protective group, for example t-butyl, trimethylsilyl, acetyl or benzyl.

Incidentally, some of the isoxazolines according to the invention can be obtained from other isoxazolines which are obtainable by the preceding method; for example, at the hydroxyl groups of 5,5-bis-hydroxymethylisoxazoline which is substituted in the 3-position it is possible to introduce or detach the abovementioned protective groups or for example hydroxyl and halogen or halogen and a protective group can be exchanged for each other.

The nitrile oxides required as starting materials can in turn be obtained from for example corresponding oximes or from aliphatic nitro compounds.

In this context, reference is made to Heterocycles, loc. cit. and the references cited therein and to Houben-Weyl, Methoden, 14th edition volume 10/3 page 83 and to J. Org. Chem. 28 (1963), 1150. Specific aspects of the asymmetrical induction in this isoxazoline synthesis have been dealt with by Jäger and Schohe (Tetrahedron Lett. 24 (1983), 5301–04).

The isolation of the nitrile oxides of the formula II is not absolutely necessary. They are advantageously produced straight away in the presence of the alkenyl compounds with which they react immediately to give the isoxazolines of the formula II.

The nitrile oxides used for preparing the isoxazolines and the alkenyl compounds can be used in equimilar ratios or can each be used in excess over the other reactant.

Suitable solvents for the reaction are for example the specific alkenyl compound itself, aromatic compounds (for example benzene, toluene or xylene), halogenated aromatic compounds, ketones (for example acetone, methyl ethyl ketone or diisopropyl ketone), ethers (for example dioxane, diethyl ether or THF) or chlorinated aliphatic hydrocarbons (for example dichloroethane, chloroform or methylene chloride).

It is noteworthy that the course of the addition of the olefins onto these nitrile oxides depends on the nature of the substituents and therefore that in certain circumstances isomers or mixtures of isomers are likely. A likely general rule is that the side of the olefinic bond which is added onto the oxygen atom of the nitrile oxide is that side which carries the bulkier substituent.

All the reactions described above usually proceed at an adequate rate below about 150° C.

A further way of obtaining isoxazolines is revealed by Preparative Example 2 below.

PREPARATIVE EXAMPLE 1 FOR AN ISOXAZOLINE

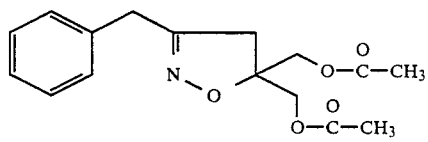

159 g of phenylacetaldoxime and 202.5 g of isobutylene diacetate are dissolved in 500 ml of diethyl ether, and 1050 ml of a 10% strength sodium hypochlorite solution are added to the vigorously stirred solution at from 10° to 15° C. Stirring is continued for several hours, after which the organic phase is extracted by shaking with water, dried over sodium sulfate and freed from the solvent.

The yield is 333 g ( ≙ 92.8% of theory). Crystals obtained by crystallization from ethanol/petroleum ether melt at 78°-79° C.

PREPARATIVE EXAMPLE 2 FOR AN ISOXAZOLINE 1960 g of 10% strength NaOH solution are added a little at a time to 200 g of allyl acetate and 242 g of 2-methylbutyraldoxime in 600 g of methylene chloride, and the mixture is stirred for 3 hours at room temperature. The organic phase is separated off, washed with water, dried over $Na_2SO_4$ and filtered, and the filtrate is freed from the solvent. The oil which remains (339 g) is 3-sec.-butyl-5-acetoxymethylisoxazole.

300-MHz-NMR spectrum in $CDCl_3$ (ppm): 0.95 (3H); 1.08 (3H); 1.2-1.3 (2H); 2.04 (3H); 2.3 (1H); 2.35 (1H); 3.0 (1H); 4.0-4.1 (2H); 4.4 (1H).

PREPARATIVE EXAMPLE 1 FOR A FURAN 88.4 g of 3-benzyl-5,5-bis-(hydroxymethyl)-isoxazoline are taken up in 550 ml of tetrahydrofuran, 40 ml of water and 80 ml of glacial acetic acid, and 1.6 g of platinum oxide are added. When hydrogen is passed in, a slightly exothermic reaction takes place. When absorption of hydrogen is complete, the mixture is filtered, the filtrate is evaporated down and the residue is stirred with acetone. The undissolved ammonium acetate is filtered off, the filtrate is evaporated down again, and the residue in 300 ml of methylene chloride is then stirred with 300 ml of 10% strength hydrochloric acid for 1 hour at 20° C. Thereafter, the solution in methylene chloride is separated off, washed with water and evaporated down to give 59.2 g (79%, based on isoxazoline) of 2-benzyl-4-hydroxymethylfuran, which is virtually pure according to NMR spectroscopy. Distillation (125°-128°/0.3 mm) gives 52.0 g of a substance having a melting point of 37°-38° C.

PREPARATIVE EXAMPLE 2 FOR A FURAN 100 g of 3-sec.-butyl-5-acetoxymethylisoxazole in 400 g of methanol and 27 g of water are hydrogenated at 20°-30° using 25 g of Raney nickel. Thereafter, the mixture is filtered and the filtrate is freed from the solvent and distilled. The liquid which distils over at 70°-80° C. is 2-sec.-butylfuran. 200 MHz-NMR spectrum in $CDCl_3$ (ppm): 0.9 (3H); 1.25 (2H); 1.5-1.8 (2H); 2.78 (1H); 6.0 (1H); 6.3 (1H); 7.35 (1H).

Other isoxazolines can be prepared from appropriate starting materials, using the above methods. For example, the substances listed in the Table below have been prepared, these substances giving an idea of the versatility of the novel process and of the active ingredients and their intermediates which are obtainable by means of this process.

| $R^1$ | $R^2$ | $R^3$ | $R^4$ | X | |
|---|---|---|---|---|---|
| $CH_3$ | H | 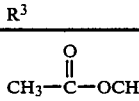 $CH_3-\overset{O}{\underset{\|}{C}}-OCH_2$ | H | $CH_3-\overset{O}{\underset{\|}{C}}-O$ | $Kp_{0.25} = 133-136°$; $M_{D25} = 1.4572$ |
| $C_2H_5-OOC$ | H | $CH_3-\overset{O}{\underset{\|}{C}}-OCH_2$ | H | $CH_3-\overset{O}{\underset{\|}{C}}-O$ | 80 MHz-NMR in $COCl_3$(ppm): 1.4(3H); 2.15(6H); 3.2(2H); 4.2-4.6(6H); |
| 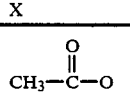 | H | $CH_3-\overset{O}{\underset{\|}{C}}-OCH_2$ | H | $CH_3-\overset{O}{\underset{\|}{C}}-O$ | Fp = 79-80° C. |
| 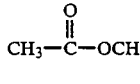 -$CH_2$ | H | $CH_3-\overset{O}{\underset{\|}{C}}-OCH_2$ | H | $CH_3-\overset{O}{\underset{\|}{C}}-O$ | Fp = 78-79° C. |
| 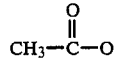 -$CH_2$ | H | $CH_2-OH$ | H | OH | Fp = 68-74° C. |
| $CH_3-OCH_2$ | H | $CH_3$ | H | $CH_3-\overset{O}{\underset{\|}{C}}-O$ | $Kp_{0.2} = 107-110°$ C. |
|  (Cl, Cl) -$CH_2$ | H | $CH_3-\overset{O}{\underset{\|}{C}}-OCH_2$ | H | $CH_3-\overset{O}{\underset{\|}{C}}-O$ | 200 MHz-NMR in $COCl_3$ (ppm) 2.06(6H); 2.8(2H); 3.81(2H) 4.16(4H); 7.25(2H); 7.43(1H). |
| F-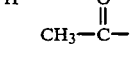-$CH_2$ | H | $CH_2OH$ | H | OH | Fp = 93-97° C. |

-continued

| $R^1$ | $R^2$ | $R^3$ | $R^4$ | X | |
|---|---|---|---|---|---|
| 3-CF$_3$-C$_6$H$_4$-CH$_2$ | H | CH$_3$-C(=O)-OCH$_2$ | H | CH$_3$-C(=O)-O | 300-MHz-NMR in COCl$_3$ (ppm) 2.01(6H); 2.8(2H); 3.75(2H); 4.04–4.23(6H); 7.4–7.68(4H). |
| C$_6$H$_5$-CH(CH$_3$)-CH$_2$ | H | CH$_3$-C(=O)-OCH$_2$ | H | CH$_3$-C(=O)-O | 300-MHz-NMR in COCl$_3$ (ppm) 1.53(3H); 2.0(3H); 2.03(3H); 2.71(2H); 3.82(1H); 4.12(2H); 4.15(2H). |

We claim:

1. An isoxazoline of the formula II

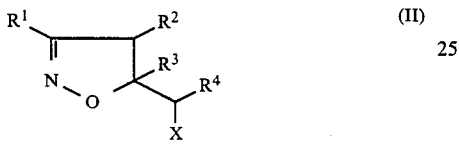

(II)

in which
R$^1$ is benzyl or benzyl substituted by halogen,
R$^2$ is hydrogen,
R$^3$ is hydroxymethyl or hydroxymethyl which is blocked by a protective group selected from the group consisting of t-butyl, trimethylsilyl, acetyl or benzyl,
R$^4$ is hydrogen or methyl,
X is hydroxy, halogen or hydroxy blocked by a protective group selected from the group consisting of t-butyl, trimethylsilyl, acetyl or benzyl.

2. A compound of the formula II as defined in claim 1, wherein
R$^1$ is benzyl,
R$^2$ and R$^4$ are each hydrogen,
R$^3$ is hydroxymethyl or hydroxymethyl which is blocked by a protective group selected from the group consisting of t-butyl, trimethylsilyl, acetyl or benzyl,
X is hydroxy, halogen or hydroxy blocked by a protective group selected from the group consisting of t-butyl, trimethylsilyl, acetyl or benzyl.

3. A compound of the formula II as defined in claim 1, wherein
R$^1$ is benzyl,
R$^2$ and R$^4$ are each hydrogen,
R$^3$ is hydroxymethyl or acetoxymethyl,
X is hydroxy, halogen or hydroxy blocked by a protective group selected from the group consisting of t-butyl, trimethylsilyl, acetyl or benzyl.

* * * * *